United States Patent [19]

Friese et al.

[11] 4,221,650

[45] Sep. 9, 1980

[54] SOLID ELECTROLYTE OXYGEN SENSORS

[75] Inventors: Karl-Hermann Friese; Friedrich J. Esper, both of Leonberg; Heinz Geier, Gerlingen, all of Fed. Rep. of Germany

[73] Assignee: Robert Bosch GmbH, Stuttgart, Fed. Rep. of Germany

[21] Appl. No.: 910,385

[22] Filed: May 30, 1978

[30] Foreign Application Priority Data

Mar. 9, 1978 [DE] Fed. Rep. of Germany ....... 2810134

[51] Int. Cl.² ............................................ G01N 27/58
[52] U.S. Cl. .................................. 204/195 S; 106/57
[58] Field of Search .............. 106/57; 204/1 S, 195 S; 429/193; 324/29

[56] References Cited

U.S. PATENT DOCUMENTS

| | | | |
|---|---|---|---|
| 2,746,874 | 5/1956 | Whittemore | 106/57 |
| 2,842,447 | 7/1958 | Schlotzhauer et al. | 106/57 |
| 2,905,564 | 9/1959 | Roup et al. | 106/57 |
| 3,454,385 | 7/1969 | Amero | 106/57 X |
| 3,518,100 | 6/1970 | Whittemore | 106/57 |
| 3,761,295 | 9/1973 | Hulse et al. | 106/57 X |
| 3,916,585 | 11/1975 | Barks | 106/57 X |
| 3,957,500 | 5/1976 | Pitts | 106/57 X |

FOREIGN PATENT DOCUMENTS

| | | | |
|---|---|---|---|
| 120586 | 11/1945 | Australia | 106/57 |
| 657163 | 6/1965 | Belgium | 429/193 |
| 561305 | 8/1958 | Canada | 106/57 |
| 2206216 | 8/1973 | Fed. Rep. of Germany | 204/195 S |
| 2631721 | 2/1977 | Fed. Rep. of Germany | 204/195 S |

OTHER PUBLICATIONS

A. G. Karaulov et al., Translated from Ogneupory, No. 8, pp. 52-59, Aug. 1973.

*Primary Examiner*—G. L. Kaplan
*Attorney, Agent, or Firm*—Frishauf, Holtz, Goodman & Woodward

[57] ABSTRACT

Oxygen sensors having a fine-grained stabilized cubic zirconium dioxide electrolyte contact respective electrodes. The zirconium dioxide contains between 15% and 50% by volume of $Al_2O_3$ in a crystalline state and has good mechanical and thermal properties. The oxygen sensor may have a composite zirconium dioxide solid electrolyte element. The invention also includes a wider range of related $Al_2O_3$- containing stabilized cubic zirconium dioxides containing between about 8% and 85% by volume $Al_2O_3$. The invention further provides methods of manufacturing such $Al_2O_3$- containing zirconium dioxide and for manufacturing oxygen sensors.

11 Claims, 1 Drawing Figure

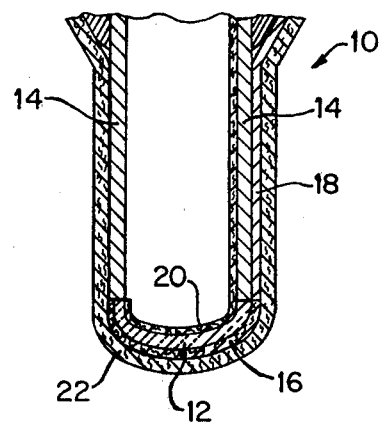

SOLID ELECTROLYTE OXYGEN SENSORS

BACKGROUND OF THE INVENTION

Stabilized zirconium dioxide is known for a variety of uses, particularly those in which it functions as a solid electrolyte. Such uses include oxygen concentration cells and fuel cells as disclosed in Vielstich's book, *Fuel Cells*, published by Wiley Interscience (English translation copyrighted 1970), pp. 248–261. Zirconium dioxide $ZrO_2$ exists in three crystal forms, i.e., the cubic form stable at high temperatures, the tetragonal also stable at high temperature, and the monoclinic which is stable at low temperatures. Since transition between these different crystal habits caused by temperature change result in volume change, parts formed from zirconium dioxide are subject to cracks and breaks when subject to a large temperature change, particularly a rapid change. It is, therefore, necessary and common practice to stabilize the cubic high temperature form completely or partially by adding at least one stabilizing oxide, a number of which are known, for example, $CaO$, $Y_2O_3$, and $Yb_2O_3$. Such stabilization minimizes or eliminates the phase changes when subjected to a change in temperature and also the resulting volume changes, so that parts formed from such stabilized zirconium dioxide have substantially greater stability.

It is necessary to sinter zirconium dioxide which is being stabilized by incorporation of one of the said stabilizer oxides at high temperatures because the diffusion of the reacting component is impeded in cubic zirconium dioxide. As a result of this high-temperature sintering, the sintered composition has a coarse-grain structure with unsatisfactory mechanical properties. It is possible to lower the sintering temperature by incorporating small quantities of sintering aids, for example, less than 5 mol %. However, the structure of even such zirconium dioxide is still relatively coarse and, consequently, the mechanical properties are not entirely satisfactory. Alumina, silica, and silicates are examples of such known sintering aids. When silica containing sintering aids are used, the high temperature strength of the zirconium dioxide ceramic product is particularly impaired.

It is known to produce fine-grained zirconium dioxide by incorporating 5 mol % $Y_2O_3$ to form a partially stabilized zirconium dioxide which sinters to form dense product at low temperatures. Molded products made from such partially stabilized zirconium dioxide exhibits superior mechanical properties. However, their crystal structure may be damaged by irreversible phase transition from the meta-stable tetragonal zirconium dioxide to the monoclinic zirconium dioxide, particularly when exposed to service conditions having repeated temperature changes. This can ultimately result in fracture of such molded products.

It is an object of the present invention to provide a fine-grained stabilized zirconium dioxide ceramic having superior mechanical properties and oxygen sensors utilizing said zirconium dioxide ceramic.

THE INVENTION

The present invention provides oxygen sensors utilizing a fine-grained stabilized cubic zirconium dioxide having good mechanical and thermal properties as the solid electrolyte separating the electrodes. The stabilized cubic zirconium dioxide contains between 15% by volume and 50% (preferably up to 40%) $Al_2O_3$. The stabilized cubic zirconium dioxide is disclosed in more detail hereinafter. The oxygen sensors are particularly useful in monitoring the oxygen content of exhaust gases from internal combustion engines as part of a control system for controlling the fuel-oxygen mixture and burning process.

The present invention also provides shaped bodies, particularly solid electrolytes useful in an oxygen sensor. A preferred solid electrolyte is in the form of a closed ended tube wherein one portion of the tube, preferably the closed end portion adapted to contact the oxygen gas being monitored, is composed of a stabilized zirconium oxide which is $Al_2O_3$-free or contains a relatively low percentage of $Al_2O_3$, with the remainder of the shaped body composed of a cubic stabilized zirconium dioxide of the present invention of higher $Al_2O_3$ content.

The present invention also provides stabilized zirconium dioxide which in addition to incorporating the stabilizer oxide is intimately mixed with between about 8% and 85% by volume $Al_2O_3$. The products are fine-grained. They are particularly useful as solid electrolytes when they contain between about 15 and 50% by volume $Al_2O_3$. It is also preferred that the zirconium dioxide be prepared from powdered $Al_2O_3$ which has a specific surface of more than 1 $m^2/g$. The zirconium dioxide is preferably stabilized with between about 5 and 30 mol % of a trivalent stabilizer oxide or between about 10 and 30 mol % of a divalent stabilizer oxide. When mixtures of di- and trivalent stabilizers are used, the preferred minimum mol percentage is between 5 and 10% depending upon the relative amounts of trivalent and divalent stabilizers utilized.

The $Al_2O_3$ admixture may be provided in whole or in part by an anhydrous crystalline alumina-containing material other than alumina itself, such as mullite or magnesium spinel, and the crystalline alumina-containing admixture can be formed in place from hydrated material such as kaolin or talc during sintering, in the case of talc by reaction with alumina.

The present invention also provides methods for producing the $Al_2O_3$-containing stabilized cubic zirconium dioxide of the present invention.

BRIEF DESCRIPTION OF THE DRAWINGS

The FIGURE illustrates a cross-sectional view of an oxygen sensor element.

DETAILED DESCRIPTION OF THE INVENTION

The generally known stabilizer oxides such as those disclosed in Vielstich and the articles referred to therein, and the work of Strickler and Carlson, reported in part in J. Am. Ceramic Soc., 48, 286–289, June 1965, and the so-called yttrium concentrate containing oxides of rare earth elements (A. K. Kuznetsow et al. in Refractories 1971 (No. 6) p. 393–395), etc., may be used as the stabilizer oxide component of the stabilized zirconium dioxide of the present invention, and preferably $Y_2O_3$, $Yb_2O_3$, $CaO$ or mixtures thereof, or mixtures of $CaO$ and $MgO$.

It is a significant feature of the zirconium dioxide of the present invention that the addition of finely ground $Al_2O_3$ in a crystalline anhydrous state impedes the grain growth so that the products may be produced with a fine-grained structure. As a consequence, the zirconium dioxide compositions of the present invention have high mechanical strength and good resistance to thermal shock. Additionally the addition of Al$_2$O$_3$ results in an increase in the heat conductivity of the product and a decrease in the coefficient of heat expansion, with the consequent additional contribution to the thermal shock resistance.

When good O$^{2-}$-ion conductivity is a desirable and necessary characteristic for the desired use of the zirconium dioxide, the quantity of Al$_2$O$_3$ incorporated therein is maintained within certain limits, generally between about 15 and 50% by volume and preferably below about 40% by volume.

The foregoing is illustrated in the case of a completely stabilized zirconium dioxide containing 7.5 mol % of Y$_2$O$_3$ and 92.5 mol % of zirconium dioxide. When a mix is prepared with the same relative amount of Y$_2$O$_3$ and ZrO$_2$, by admixing thereto 40% by volume of alumina, the O$^{2-}$-ion conductivity is reduced so that it is about equal to that of a partially stabilized ceramic of 5 mol % Y$_2$O$_3$ and 95 mol % ZrO$_2$ which does not contain Al$_2$O$_3$. If the same composition is varied by adding an amount greater than 50% by volume of alumina, the O$^{2-}$-ion conductivity of the product which is a completely stabilized zirconium dioxide decreases at an accelerated rate.

The reduction in electrical conductivity which results from the addition of alumina to a zirconium dioxide stabilized with Y$_2$O$_3$, can be partially compensated for by replacing Y$_2$O$_3$ with Yb$_2$O$_3$.

The Al$_2$O$_3$ component of the alumina-containing finegrained zirconium dioxide of the present invention may be partially or completely provided by alumina-containing compounds of high thermal stability, for example magnesium spinel (MgO·Al$_2$O$_3$), and mullite (3 Al$_2$O$_3$·2SiO$_2$). Such thermally stable anhydrous alumina-bearing crystalline materials may be admixed with the other powdered components of the compositions of the present invention in finely ground form, e. g. the finely ground precalcinated material or as the finely ground product of a fusion process. It is also possible to incorporate such anhydrous crystalline alumina-contributing components to the final product by admixing with the zirconium dioxide and the stabilizer oxide, hydrated materials which during the sintering process generate (form) the desired anhydrous crystalline alumina-containing compound, for example kaolin may be used which reacts to form mullite, and talc may be used which reacts with Al$_2$O$_3$ to form the magnesium spinel. The use of kaolin, talc and other such raw materials having plasticizing characteristics may improve the formability of the raw mixture of powders. When a desired alumina-containing material is formed in situ during the sintering process as aforesaid, consideration should be given to the other oxides contributed by the raw materials so that they will not include materials which adversely effect the desired characteristics of the stabilized zirconium dioxide product beyond a possible amount which may be tolerated.

Not only alumina but also magnesium spinel and mullite are primarily utilized in the compositions of the present invention because during sintering these materials functions to impede grain growth in the composition, and further because the alumina can be introduced on an industrial scale with available technology, and may be available as a commercial product.

The processing of the raw mixtures and particularly the green molding and/or other forming is aided by the incorporation of small amounts of plasticizer materials, for example not more than 10% by weight. Certain of the plasticizing materials include substances which have an adverse effect on the high temperature properties of the product, for example silica which is a component of talc. Plasticizers which include substances which may adversely effect the desired properties of the stabilized zirconium dioxide of the present invention should be avoided as much as possible, particularly if the zirconium dioxide is to be heated to temperatures above 1000° C.

Generally raw materials contain impurities of various types. It is desired that impurities, such as, for example, Fe$_2$O$_3$, P$_2$O$_5$, SO$_3$, Na$_2$O, B$_2$O$_3$, be maintained below 1% of the total mixture of raw materials. However, HfO$_2$ which is often co-present with ZrO$_2$ may be present in the usual amounts, that is, less than about 5% by weight of the ZrO$_2$.

The sinter activity of the ceramic mixture which forms the Al$_2$O$_3$-containing stabilized zirconium dioxide of the present invention is not changed, relative to a similar composition without the Al$_2$O$_3$, if the Al$_2$O$_3$ raw material added is of a fine particle size, preferably having a specific surface of more than 1 m$^2$/g, and when these powdered components are thoroughly admixed.

The powdered components which are mixed to form the raw powder mixture which is then sintered, may be formed from powdered oxides each of which has been comminuted to the desired small particle size prior to mixing. It is however advantageous to mix coarser particles of the oxides, that is the Al$_2$O$_3$, the stabilizer (e.g. Y$_2$O$_3$) and the ZrO$_2$ and then grind the mixture to the desired small particle size. The mixture may also be prepared by mixing the oxides and then calcining them to form a heterogeneous mixture of fully or partially stabilized zirconia grains and of Al$_2$O$_3$-grains and then grinding them into the desired small particle size, preferably less than 1 μm. The mixed finely ground powders are processed to form the stabilized zirconia bodies by the usual ceramic processing techniques, for example granulating or plasticizing; compacting, extruding, form-grinding, or thermoplastic molding; followed by sintering, pressure sintering, or hot pressing.

Shaped alumina-containing stabilized zirconium dioxide compositions may be integrally formed from at least one stabilized zirconium dioxide component containing alumina and another such component which does not or which contains different amounts of alumina. When forming such integral components from at least two different compositions, it is necessary that each of the components must have an approximately equal amount of shrinkage during the forming process particularly sintering. This can be controlled by the degree of pulverization of the raw materials and by varying the processing aids and particularly the usual organic processing (pressing or extruding) aids such as those exemplified hereinafter.

The FIGURE illustrates an example of such a shaped composite stabilized zirconium dioxide body as a component of an oxygen sensor 10. The oxygen sensor is formed around a composite zirconium dioxide body in the form of a closed ended tube having a cylindrical portion 14 and a closed ended rounded or domed portion 12. The closed ended section 12 is formed from a highly O$^{2-}$-ion conductive stabilized zirconium dioxide, for example stabilized with Y$_2$O$_3$. Portion 12 may contain a small amount of Al$_2$O$_3$ insufficient to substantially interfere with the O$^{2-}$-ion conductivity. Portion 14 is formed from the alumina-containing stabilized zirconium oxide of the present invention, containing, e.g., 50% by volume alumina. It is fine-grained and has good mechanical strength at high temperatures. The oxygen sensor of FIG. 1 contains an inner electrode 20 located on the inside of the tube, for example a conductive porous electrode and a connecting strip made of a noble metal or other material which is electron conductive at the operating temperature of the oxygen sensor. The outer surface of the solid electrolyte 12 is at least partially covered by a catalytically active porous electrode 16, for example platinum. The electrode 16 is connected by a conductive strip 18 along the tube to an electrical measurement device. The outer surface of the sensor and particularly that portion adapted to contact automobile exhaust gases is preferably coated with a porous insulating coating 22, for example of magnesium spinel as disclosed in U.S. Pat. No. 4,021,326. This composite oxygen sensor may be used under conditions in which there is a faster warm-up time to reach the temperature at which it operates. It has the additional advantage that when the cylindrical portion 14 has a high alumina content, it has substantially lower conductivity which minimizes the possibility of an internal short circuit between (i) the electrode 20 and (ii) the continuation of electrode 16 or a conductive strip 18 located respectively on the inner and outer surfaces of the solid electrolyte as described in DE-OS 25 04 207. Such composite sensors may be prepared by the methods disclosed in application Ser. No. 868,627 filed Jan. 11, 1978 and now U.S. Pat. No. 4,152,234.

A sensor having the form of sensor 10 except that it is not a composite may be formed wherein both the end portion 12 and the cylindrical portion 14 of the stabilized zirconium dioxide are formed from an $Al_2O_3$-containing stabilized zirconium dioxide having sufficient $O^{2-}$-ion conductivity to function as an oxygen sensor, e.g., one prepared from the composition of Example 1. The $Al_2O_3$-containing stabilized zirconium dioxide of the present invention may also be used as the solid electrolyte in oxygen sensors wherein both electrodes are contacted with the exhaust gas, e.g., those disclosed in German application P 27 18 907.7 filed Apr. 28, 1977 which is incorporated by this reference. All of the sensors of the present invention are particularly useful for monitoring the oxygen content of the exhaust gases from internal combustion engines.

The $Al_2O_3$-containing zirconium dioxide of the present invention may be completely stabilized as disclosed hereinbefore and such sintered compositions have a fine-grained structure so that their shaped parts have high mechanical properties which are comparable to the high properties which could heretofore be obtained with partially stabilized zirconium dioxide, without the disadvantages associated with partially stabilized zirconium dioxide, i.e., the possibility of irreversible phase transition under service conditions involving repeated temperature reversals.

Although the noted advantages of the $Al_2O_3$-containing zirconium dioxide is particularly stressed in connection with fully stabilized zirconium dioxide, small amounts of non-stabilized zirconium dioxide may be tolerated. This is particularly the possibility if the composition contains only small amounts of monoclinic or tetragonal $ZrO_2$ which are not sufficient to adversely affect the integrity of the sintered composition during service. Small quantities of such non-stabilized $ZrO_2$ may be advantageous in that they tend to improve the sinter activity of the mixture of powdered oxides which are sintered to form the $Al_2O_3$-containing zirconium dioxide of the present invention.

The use of alumina as a raw material has the additional advantage that the alumina is less expensive than zirconia raw materials of the desired degree of purity and particle size. As a consequence, the use of alumina as a component of the product in the largest amount possible consistent with the desired properties results in a lowering of the raw material cost.

The invention is further illustrated in the following illustrative Examples:

EXAMPLE 1

The following raw materials were utilized:

$ZrO_2$ raw material containing at least 99.5% by weight $ZrO_2$ containing approximately 2% by weight $HfO_2$ with a specific surface of 3 $m^2/g$. $Y_2O_3$ raw material containing at least 99% by weight $Y_2O_3$ with impurities being predominantly oxides of rare earth metals and with a specific surface of 3 $m^2/g$; with remaining impurities less than 0.5%. $Al_2O_3$ raw material being 99.5% $Al_2O_3$ having a specific surface more than 1 $m^2/g$, which is pre-ground if necessary to obtain this particle size.

The $ZrO_2$ is in an amount of 59.2% by weight; the $Y_2O_3$ in an amount of 8.8% by weight and the $Al_2O_3$ in an amount of 32.0% by weight. The mol ratio of $ZrO_2$ and $Y_2O_3$ is 0.95:0.075. The foregoing corresponds to approximately 60% by volume of the total of $ZrO_2$ and $Y_2O_3$, and 40% by volume of $Al_2O_3$.

The powders were premixed until a uniform mixture was obtained. The mixture was then ground in a ball mill to reach an average particle size of less than 1 $\mu m$. The ball milled mixture was then granulated with an organic binder, 1% by weight of an emulgated wax binder or 0.5% by weight polyvinyl alcohol as usual for granulation of oxide ceramic powders. The method for manufacturing the oxygen sensor is described in detail in U.S. Pat. No. 3 978 006. An oxygen sensor was made from this ceramic material and has been tested with good results.

The granulated mixture was then pressed to form a green compact which was then sintered in an oxidizing atmosphere at a temperature between 1400° C. and 1650° C.

EXAMPLE 2

A mixture of $ZrO_2$ and $Y_2O_3$ having the same mol ratio as in Example 1 were mixed and ground to reach a particle size less than 1 $\mu m$. This was then calcined in bulk form in a calcining oven at a temperature between 1200° C. and 1500° C. The calcined mixture was then crushed and ground to a particle size of less than 1 $\mu m$. This was then admixed with finely ground $Al_2O_3$; 32% of $Al_2O_3$ and 68% by weight of said ground calcined mixture of $ZrO_2$ and $Y_2O_3$. The powders were thoroughly admixed and then processed as Example 1. An oxygen sensor made of this ceramic material was operative.

EXAMPLE 3

A mixture was formed as in Example 1 except that 40% by volume of $MgO \cdot Al_2O_3$ was used in place of the $Al_2O_3$ of Example 1. The approximately 40% by volume of $MgO \cdot Al_2O_3$ corresponded to a weight percentage of 26.08%. The 60% by volume of the same mol ratio mixture of $ZrO_2$ and $Y_2O_3$ corresponds to a weight percent of 64.35% $ZrO_2$ and 9.57% $Y_2O_3$. The MgO- ·Al$_2$O$_3$ consisted of more than 95% by weight of MgO·Al$_2$O$_3$, with the remainder being α-Al$_2$O$_3$, MgO and CaO·6Al$_2$O$_3$; with other impurities being less than 0.5% by weight. The powdered materials were prepared and the mixture prepared and then processed to form the sintered product, following the procedures of Example 1. An oxygen sensor made of this ceramic material has been tested with good results.

EXAMPLE 4

The procedures of Example 1 were followed using 58.7% by weight ZrO$_2$, 9.3% of a Y$_2$O$_3$ concentrate, and 32% Al$_2$O$_3$. The Y$_2$O$_3$ concentrate contained 60% by weight Y$_2$O$_3$ with the remainder mainly oxides of rare earth elements, with other impurities being less than 1%. An oxygen sensor made of this ceramic material was operative.

EXAMPLE 5

30 weight % of Al$_2$O$_3$ which corresponds to 40 volume % was admixed with 55.6 weight % ZrO$_2$ and 14.4 weight % Yb$_2$O$_3$. The ZrO$_2$ and Yb$_2$O$_3$ are in a mol ratio of 0.95:0.075 with the total of both corresponding to 60 volume % of the total mixture. The Yb$_2$O$_3$ raw material contained at least 99% Yb$_2$O$_3$ by weight with the remainder mainly oxides of rare earth elements and Y$_2$O$_3$, with other impurities being less than 0.5%. The composition was processed following the procedure of Example 1.

EXAMPLE 6

67% by weight of a total of ZrO$_2$ and CaO (present in a mol ratio of 0.9:0.1) and 33 weight % of Al$_2$O$_3$ were mixed. The Al$_2$O$_3$ raw material was the same as that described in Example 1. The 90:10 mol ratio mixture of ZrO$_2$ and CaO were produced by arc melting, which was then broken and ground to a particle size of less than 5 μm, with impurities totaling less than 1% by weight. The powders were processed following the procedures of Example 1, except that sintering is carried out at a temperature of between 1500° and 1750° C. The powders may also be processed following Example 1, except that they are compressed at temperatures between 1100° C. and 1300° C. at a pressure of 500 bar.

EXAMPLE 7

A powder mixture was produced composed of 59.2% ZrO$_2$ by weight, 8.8% Y$_2$O$_3$, 26.0% Al$_2$O$_3$, and 6% kaolin. The kaolin raw material contained in excess of 95% pure kaolinite (Al$_2$O$_3$·2SiO$_2$·2H$_2$O) with, in addition to the Al$_2$O$_3$ and SiO$_2$, impurities totaling less than 1% by weight. These powders were processed following the procedures of Example 1.

EXAMPLE 8

Al$_2$O$_3$ in an amount of 32% by weight which corresponds to approximately 40% by volume were admixed with a 60% by volume of a total of ZrO$_2$ and Y$_2$O$_3$. The ZrO$_2$ was present in an amount of 60.9% by weight and the Y$_2$O$_3$ in an amount of 7.1% which corresponds to a mol ratio of 0.94:0.06. The materials were processed following the procedures of Example 1 to form the sintered ceramic product. Because of the relatively low content of Y$_2$O$_3$, a portion of the ZrO$_2$ in the sintered product was not stabilized.

EXAMPLE 9

Al$_2$O$_3$ in an amount of 6% by weight which corresponds to approximately 8% by volume was admixed with ZrO$_2$ and Y$_2$O$_3$ which together constituted the remaining approximately 92% by volume. The ZrO$_2$ was in an amount of 81.85% by weight and the Y$_2$O$_3$ in an amount of 12.15% which corresponds to a mol ratio of 0.925:0.075. The raw materials were processed to form the sintered product following the procedure of Example 1.

EXAMPLE 10

Al$_2$O$_3$ in an amount of 75% by weight which corresponds to approximately 85 volume % was admixed with approximately 15 volume % of the total of ZrO$_2$ and Y$_2$O$_3$. The ZrO$_2$ was in an amount of 21.75% by weight and the Y$_2$O$_3$ in an amount of 3.25% which represents a mol ratio of 0.925:0.075. The raw materials were processed to form the sintered product following the procedures of Example 1.

Molded sintered objects prepared in accordance with the procedures of the foregoing Examples were subjected to various test procedures of which the bending strength tests and the test for resistance to thermal shock are of the greatest interest. The bending strength was determined by applying radial loading to ring-shaped specimens as described in the book "Mechanical Properties of Engineering Ceramics", ed. by W. W. Kriegel et al., 5.383 H, Interscience Publishers, New York, 1969. An acoustic emission analysis was used to determine resistance to thermal shock by one-sided chilling of the specimens by applying a cold air stream against the specimen resulting in the specimen being heated at a linear rate of increase of temperature. The test utilized periodic cooling cycles. This method is described by F. J. Esper et al. in "Ber. dt. Keram. Ges.", to be published. The results of the foregoing tests were compared with the results of the same tests applied to partially stabilized zirconium dioxide of the prior art. The test results establish that the sintered shaped objects of the present invention displayed the same bending strength as shaped objects prepared from the sintered partially stabilized ceramic of the prior art. The mechanical strength of the completely stabilized zirconium dioxide of the present invention obtained by including in the composition as little as 8% by volume Al$_2$O$_3$ is approximately equal to the mechanical strength of the partially stabilized ZrO$_2$. However, the resistance to thermal shock of the completely stabilized zirconium dioxide of the present invention only becomes approximately comparable to the thermal shock resistance of the partially stabilized zirconium dioxide of the prior art when the completely stabilized Al$_2$O$_3$-containing zirconium dioxide of the present invention contains at least 15% by volume Al$_2$O$_3$. However, the structural stability of the Al$_2$O$_3$-containing stabilized zirconium dioxide of the present invention is far superior to that of the partially stabilized ZrO$_2$ of the prior art.

The solid electrolyte of the invention has an electrical resistivity $\leq 10^7$ Ωcm, preferably $\leq 5.10^4$ Ωcm at the temperature of 600° C. The method of measuring this resistivity is described by L. J. van der Pauw in Philips Res. Repts. 13 (1958), p. 1–9.

The bending strength of the ZrO$_2$ ceramic material of the invention must be $\geq 250$ N/mm$^2$, preferably $\geq 350$ N/mm$^2$.

The resistance to thermoshock, expressed the temperature at which the first crack was registered as described in the above mentioned article by Esper et al, must be $\geq 650°$, preferably $\geq 800°$ C.

The following table shows the effect of the $Al_2O_3$ content of the $ZrO_2$ ceramic material on the average particle size of the cubic $ZrO_2$ in the ceramic material and on the resistance to thermal shock. The specimens were prepared by mixing 92.5% by volume $ZrO_2$ with 0.075% by volume $Y_2O_3$ and then adding the amounts of $Al_2O_3$ as given in the table, the $Al_2O_3$ having a specific surface of more than 1 $m^2/g$. The further preparation was made as described above.

| Content $Al_2O_3$ (Vol %) | Average grain size of cubic $ZrO_2$ ($\mu m$) | Resistance to thermal shock t (°C.) |
|---|---|---|
| 4 | 21 | 590 |
| 7 | 12 | 660 |
| 16 | 6 | 780 |
| 22 | 3,5 | 820 |
| 32 | 1,5 | 890 |
| 41 | 1 | 900 |
| 50 | | 920 |
| 65 | <1 | 920 |
| 78 | | 920 |
| 89 | | 920 |

The table shows a decrease of the grain size of the cubic $ZrO_2$ in the ceramic correlated with an increase of the resistance to thermal shocks.

If the $ZrO_2$ is stabilized with MgO and CaO the amounts of these two oxides should preferably be in a ratio as disclosed in the German Patent application Ser. No. P 27 14 558.0 of Apr. 1, 1977. The Mg-spinel possibly used instead of or in addition to $Al_2O_3$ does not influence the stabilizing reactions of the $ZrO_2$ so that the magnesium of the Mg-spinel must not be taken into account if the $ZrO_2$ is stabilized with MgO and CaO. Up to 5 mole % of the CaO may be substituted by $Y_2O_3$ and/or $Yb_2O_3$ as also disclosed in the above cited German Ser. No. 27 14 558.0.

The composition of the $ZrO_2$ ceramic material of the invention is:

| | | |
|---|---|---|
| 1. | ($ZrO_2$ + stablizing oxide) | 92–15% by volume related to the sum of 1. and 2. |
| 2. | $Al_2O_3$ and/or anhydrous $Al_2O_3$-compounds in a crystalline state as mentioned above | 8–85% by volume, related to the sum of 1. and 2. |
| 3. | Impurities as mentioned above | zero up to 5% by weight, preferably up to 1% by weight, related to the total amount. |
| 4. | Inorganic plasticizing materials (kaolin, talc or other) | zero up to 10% by weight |

The zirconium dioxides of the present invention may be fully stabilized or may contain only sufficient stabilizer oxide to stabilize at least 40 mol % of the $ZrO_2$ and, preferably, at least 85 mol %.

Referring to the Figure the solid electrolyte 12 should not contain $Al_2O_3$ or may contain up to 50% by volume $Al_2O_3$ and/or anhydrous $Al_2O_3$-compounds, preferably up to 8% by volume, whereas the solid electrolyte 14 contains 15 to 50% by volume $Al_2O_3$ and/or anydrous $Al_2O_3$-compounds, preferably 20 to 45% by volume.

We claim:

1. An oxygen sensor particularly adapted to monitor the oxygen content of exhaust gases from internal combustion engines comprising an $O^{2-}$-ion conductive zirconium dioxide solid electrolyte in electron conductive contact with spaced electrodes, one of which is adapted to contact the exhaust gases being monitored, further comprising the improvement which consists in that said solid electrolyte consists essentially of at least partially stabilized cubic zirconium dioxide having dispersed therein between about 15% and 50% by volume of at least one anhydrous crystalline aluminum-containing oxide compound selected from the group consisting of magnesium spinel, mullite and alumina and having a specific surface of more than 1 $m^2/g$, said solid electrolyte having an electrical resistivity not exceeding $10^7$ $\Omega cm$ at a temperature of 600° C., substantially all of the material other than said aluminum-containing oxide compound consisting of said stabilized zirconium dioxide.

2. The oxygen sensor of claim 1 wherein said solid electrolyte is composed of a sintered mixture of powders wherein said solid electrolyte has an electrical resistivity not exceeding $5.10^4$ $\Omega cm$.

3. The oxygen sensor of claim 1 wherein said zirconium dioxide is completely stabilized to the cubic phase.

4. The oxygen sensor of claim 1 wherein said zirconium dioxide is partially stabilized to the cubic phase.

5. The oxygen sensor of claim 2 containing up to about 40% by volume of said aluminum containing oxide compound or compounds.

6. The oxygen sensor of any one of claims 1-4 and 5 wherein said at least partially stabilized cubic zirconium dioxide is composed of zirconium dioxide crystalline grains incorporating therein at least one stabilizer oxide selected from the group consisting of $Y_2O_3$, $Yb_2O_3$, CaO and mixtures of CaO and MgO.

7. The oxygen sensor of any one of claims 1-4 and 5 wherein said at least partially stabilized cubic zirconium dioxide is composed of zirconium dioxide crystalline grains incorporating therein at least one stabilizer oxide selected from the group consisting of $Y_2O_3$, $Yb_2O_3$, CaO and mixtures of CaO and MgO, and wherein said zirconium dioxide is stabilized by incorporation into the grains thereof of at least one stabilizer oxide in an amount of between 5 and 30 mol % of total trivalent stabilizer oxide content or between about 10 and 30 mol % total divalent stabilizer oxide content, referred to the total content of zirconium dioxide and stabilized oxide.

8. A shaped composite oxygen sensor adapted to monitor the oxygen content of exhaust gas from internal combustion engines comprising an $O^{2-}$-ion conductive stabilized cubic zirconium dioxide solid electrolyte in electron conductive contact with respective spaced electrodes, one of which is adapted to contact the exhaust gases being monitored, and having the improvement which consists in that said electrolyte is a composite solid electrolyte comprising two sections integral with each other, a first section adapted to contact the electrode which contacts the exhaust gas consisting essentially of a shpaed fine-grained stabilized cubic zirconium dioxide mass in which is interspersed between the grains of said zirconium dioxide between zero and 50% by volume of at least one anhydrous crystalline aluminum-containing oxide compound selected from the group consisting of magnesium spinel, mullite and alumina and having a specific surface of more than 7 m²/g and also good $O^{2-}$-ion conductivity, and a second section consisting essentially of a shaped fine-grained stabilized cubic zirconium dioxide mass in which is interspersed between the grains of said zirconium dioxide between about 15 and 50 by volume of a material composed of at least one anhydrous crystalline aluminum-containing oxide compound selected from said group and having a specific surface of more than 1 m²/g, said second section electrolyte having an electrical resistivity not greater than 10 $\Omega$cm at a temperature of 600° C., and when said first section electrolyte contains alumina among said compounds selected from said group, said second electrolyte section has a greater proportional content of alumina than said first section electrolyte.

9. The shaped oxygen sensor of claim 8 in the form of a tube closed at one end wherein said second section is shaped as the tubular portion of said tube and the first section is shaped as the end portion of said tube.

10. The shaped oxygen sensor of claim 8 wherein said material composed of aluminum-containing oxide interspersed between said zirconium dioxide grains of said first section is less than 8% by volume of the resulting mass.

11. The shaped oxygen sensor of either of claims 8 and 10 wherein the resistivity of said zirconium dioxide mass of said second section is not greater than $5 \cdot 10^4$ $\Omega$cm at 600° C.

* * * * *